United States Patent [19]

Takamizawa et al.

[11] Patent Number: 5,050,611
[45] Date of Patent: Sep. 24, 1991

[54] ULTRASONIC IMAGING APPARATUS

[75] Inventors: Kinya Takamizawa, Utsunomiya; Makoto Hirama; Hironobu Hongo, both of Ootawara, Japan

[73] Assignee: Kabushiki Kaisha Toshiba, Kawasaki, Japan

[21] Appl. No.: 417,023

[22] Filed: Oct. 4, 1989

[30] Foreign Application Priority Data

Oct. 5, 1988 [JP] Japan ................................ 63-251251

[51] Int. Cl.$^5$ .............................................. A61B 8/06
[52] U.S. Cl. ............................ 128/661.09; 128/660.05
[58] Field of Search ......... 128/660.05, 661.07–661.10; 73/861.25

[56] References Cited

U.S. PATENT DOCUMENTS

| | | | |
|---|---|---|---|
| 4,817,617 | 4/1989 | Takeuchi et al. | 128/660.05 |
| 4,915,115 | 4/1990 | Sasaki et al. | 128/660.05 |
| 4,918,605 | 4/1990 | Shirosaka | 128/660.05 X |

FOREIGN PATENT DOCUMENTS 0361264 4/1990 European Pat. Off. .
2579886 10/1986 France .

Primary Examiner—Francis Jaworski
Attorney, Agent, or Firm—Cushman, Darby & Cushman

[57] ABSTRACT

An ultrasonic imaging apparatus comprises an ultrasonic transducer for outputting ultrasonic beams and converting echo waves of the ultrasonic beams to a B-mode echo signal corresponding to a B-mode for obtaining a tomographic image and a D-mode echo signal corresponding to a D-mode for obtaining Doppler data, a transmitter circuit for driving the transducer for generating the ultrasonic beams for scanning a subject, a receiver circuit including a gain control circuit for controlling the gain of the B-mode and D-mode echo signals output from the ultrasonic transducer so that the level of the B-mode echo signal is made to equal to that of the D-mode echo signal and for outputting gain-controlled echo signals, and A/D converter for converting the gain-controlled signals to digital signals, and a delay/addition circuit for delaying the digital signals and adding them to output a received signal, a B-mode processor circuit for producing a B-mode image signal from the received signal, a D-mode processor circuit for producing Doppler data from the received signal, and a display for displaying the B-mode image signal and D-mode data.

17 Claims, 4 Drawing Sheets

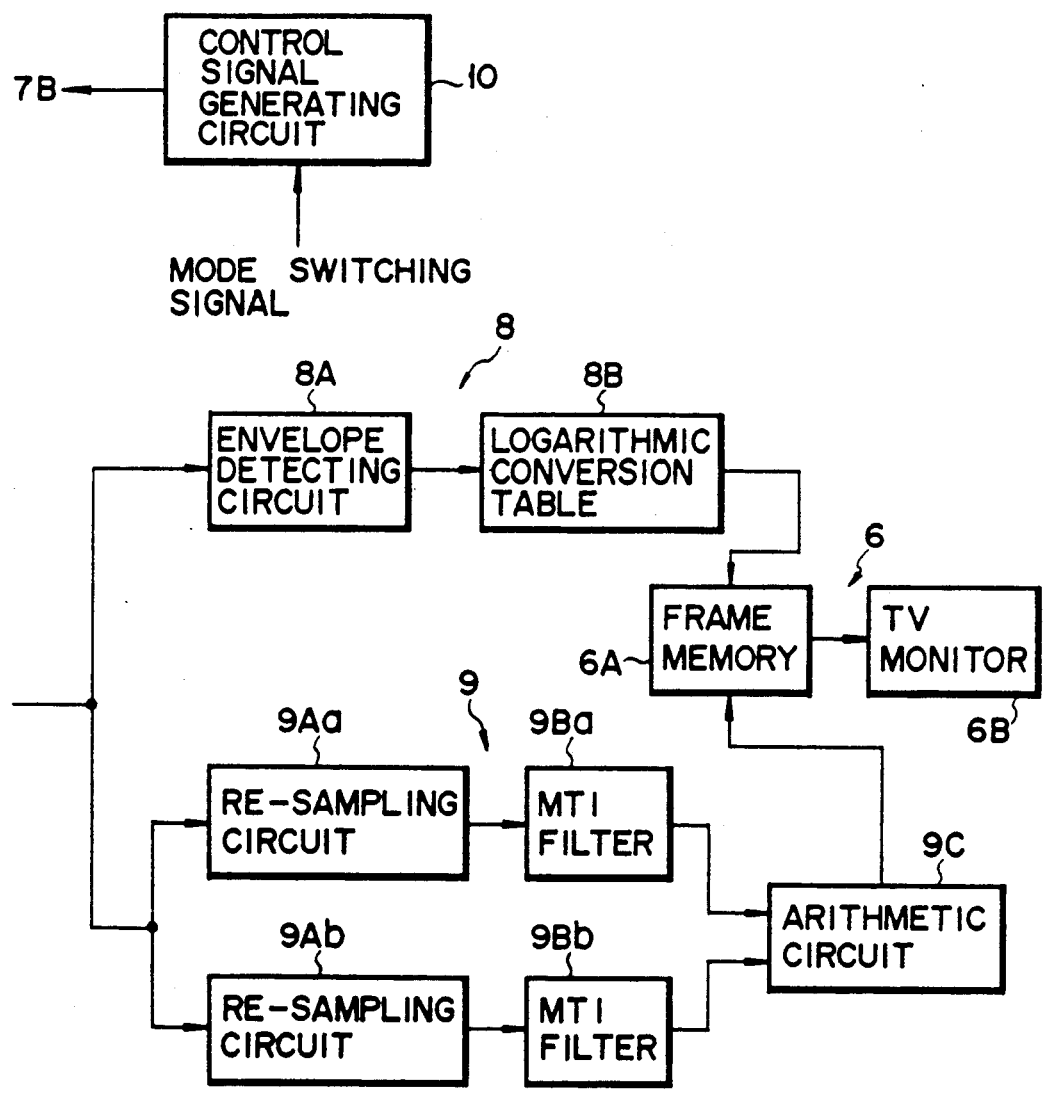
F I G. 1B

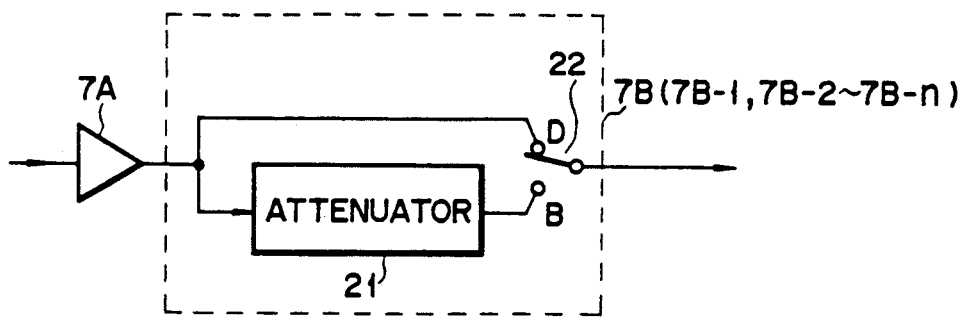
F I G. 2
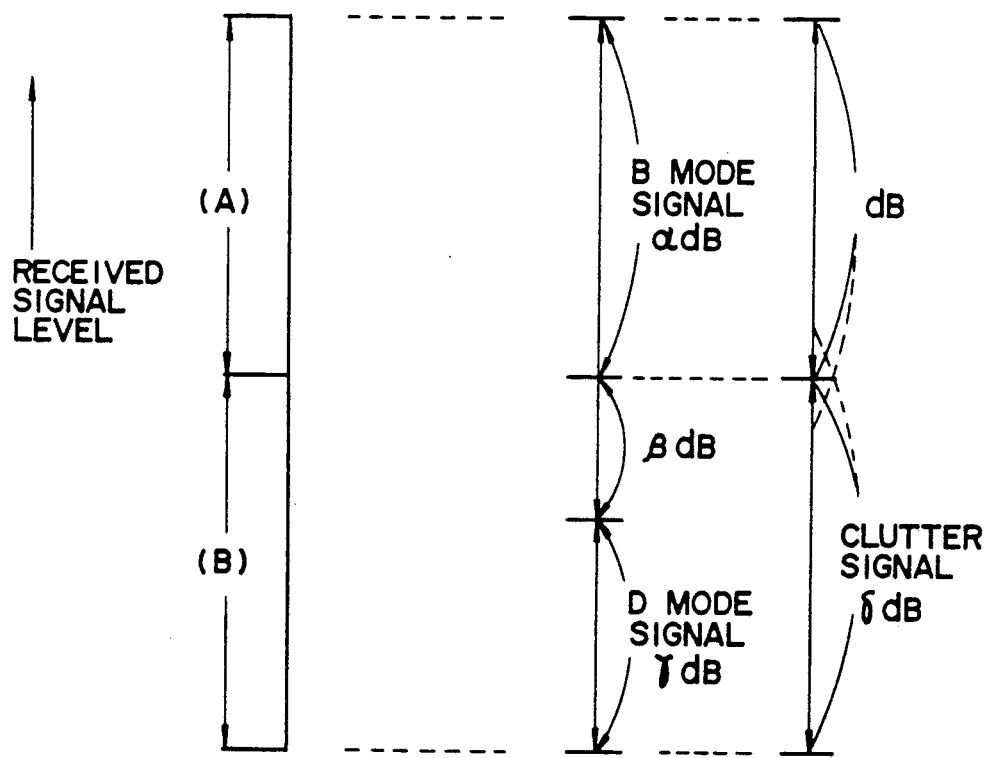
F I G. 3

ULTRASONIC IMAGING APPARATUS

BACKGROUND OF THE INVENTION

1. Field of the Invention

The present invention relates to an ultrasonic imaging apparatus, in particular, capable of selecting one of a tomographic mode (B-mode) for obtaining a tomographic image and a Doppler mode (D-mode) for obtaining blood flow data or two-dimensional blood flow image (color flow mapping image).

2. Description of the Related Art

The ultrasonic imaging apparatus is used as an ultrasonic diagnosis apparatus for scanning a subject with an ultrasonic beam to obtain a tomographic image or a blood flow image of the subject, and diagnosing the subject based on the obtained image. In order to scan the subject with the ultrasonic beam, it is necessary to converge or deflect the ultrasonic beam. As means for converging or deflecting the ultrasonic beam, delay circuits are provided in an ultrasonic transmitter circuit and an ultrasonic receiver circuit. In general, an analog delay element, for example, an LC delay element, is used as the delay circuit. However, where the LC delay element is used, it is difficult to attain a long delay, and precision of delay time is not satisfactory. In particular, if the frequency of a drive signal is increased, a sufficient delay performance is not obtainable by the LC delay element.

Under the circumstances, it has been proposed to form the delay circuit and its peripheral section in a digital manner. In this case, much consideration must be given to the use of an A/D converter. An ultrasonic signal has a wide dynamic range from a high signal level to a low signal level. An A/D converter for directly A/D converting the signal of a wide dynamic range is not generally employed and is expensive. If such an expensive A/D converter was provided in each of a great number of channels of an ultrasonic imaging apparatus, the manufacturing cost of the apparatus would increase.

SUMMARY OF THE INVENTION

The object of the present invention is to provide an ultrasonic imaging apparatus, which can perform a tomographic mode operation and a Doppler mode operation by a digital delay system, and which can cover a wide dynamic range of an ultrasonic signal by using an inexpensive narrow-dynamic range A/D converter.

According to the present invention, there is provided an ultrasonic imaging apparatus wherein a gain control circuit for controlling the gain of received signal is connected at the front stage of an A/D converter for digitizing the received signal.

An ultrasonic imaging apparatus according to the present invention comprises an ultrasonic transducer for outputting ultrasonic beams and converting echo waves of the ultrasonic beams to a B-mode echo signal corresponding to a B-mode for obtaining a tomographic image and a D-mode echo signal corresponding to a D-mode for obtaining Doppler data; a transmitter circuit for driving the transducer for generating the ultrasonic beams for scanning a subject; a receiver circuit including a gain control circuit for controlling the gain of the B-mode and D-mode echo signals output from the ultrasonic transducer so that the level of the B-mode echo signal is made to equal to that of the D-mode echo signal and for outputting gain-controlled echo signals, an A/D converter for converting the gain-controlled signals to digital signals, and a delay circuit for delaying the digital signals and outputting received signals; a B-mode processor circuit for producing a B-mode image signal from the received signals; a D-mode processor circuit for producing Doppler data from the received signals; and a display for displaying the B-mode image signal and D-mode data.

According to the present invention, in the D-mode, the amplitude of the D-mode signal is made to match with the input range of the A/D converter. Also, in the B-mode, by reducing the gain of the B-mode signal, the amplitude of the B-mode signal is made to match with the input range of the A/D converter. Thus, an A/D converter of small bit resolution, i.e., a narrow dynamic range, can be used in each receiving channel, and the tomographic image mode and Doppler mode can be performed substantially at the same time.

BRIEF DESCRIPTION OF THE DRAWINGS

FIGS. 1A and 1B show a block diagram of an ultrasonic imaging apparatus according to an embodiment of the present invention;

FIG. 2 shows a gain control circuit used in the apparatus shown in FIG. 1;

FIG. 3 shows a signal level distribution of a B-mode signal and a D-mode signal;

DETAILED DESCRIPTION OF THE PREFERRED EMBODIMENTS

Figure 1A:
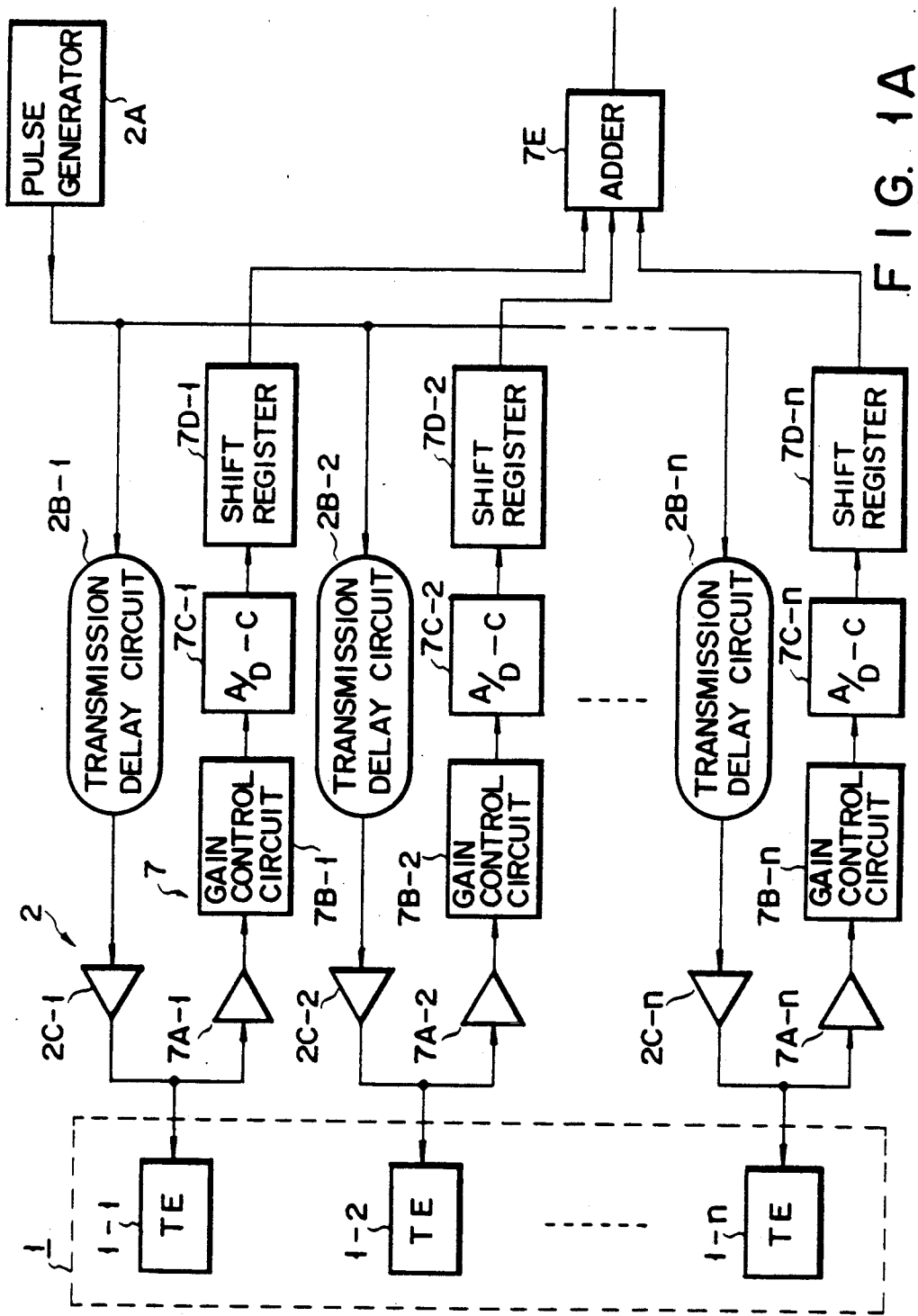

An ultrasonic imaging apparatus shown in FIGS. 1A and 1B comprises an array probe 1, a transmitter circuit 2, a digital receiver circuit 7, a B-mode processor circuit 8, a D-mode processor circuit 9, and a video processor circuit 6. The array probe 1 is constituted by an n-number of juxtaposed ultrasonic transducer elements 1—1, 1—2...1—n (n-channels). For example, the array probe 1 is operated in a sector scan mode. In other words, the transducer elements 1—1, 1—2...1—n are driven by the transmitter circuit 2 to propagate ultrasonic beams to a subject (not shown). Then, the transducer elements 1—1, 1—2...1—n receive echoes of the ultrasonic beams sent back from the subject, and supply corresponding echo signals to the digital receiver circuit 7.

The transmitter circuit 2 comprises pulse generator 2A, transmission delay circuit 2B (2B—1, 2B—2...2-B—n), and pulser 2C (2C—1, 2C—2...2C—n). The pulse generator 2 outputs to the transmission delay circuit 2B (2B—1, 2B—2...2B—n) a rate pulse (repetitive pulse) for determining the ultrasonic transmitting and receiving timings. The transmission delay circuit 2B (2B—1, 2B—2...2B—n) performs a transmission delay control, that is, varies the timings for exciting the transducer elements, from element to element, thereby to focus the transmission beam or to deflect the beams for the sector scanning. The pulser 2C (2C—1, 2C—2...2-C—n) supplies a high voltage pulse to the transducer element 1—1 (1—2...1—n) in response to a transmission delay control signal output from the transmission delay circuit 2 (2B—1, 2B—2...2B—n).

The video processor circuit 6 comprises a frame memory 6A, which constitutes a main part of a digital scan converter (DSC) for converting an ultrasonic scan to a TV scan, and a TV monitor 6B. The frame memory 6A has a memory region corresponding to one frame of a TV screen. Superposed data of tomographic data (monochromatic data) output from the B-mode processor circuit 8 and CFM (color flow map) image data (color data) output from the D-mode processor circuit 9 is written in this memory region at every ultrasonic raster. When one frame has been formed in the frame memory 6A, an image produced by superposing a CFM image on a tomographic image, or an image produced by showing blood flow data (numerical value) on the tomographic image, is displayed on the TV monitor with a standard TV format.

The digital receiver circuit 7 comprises a variable gain type preamplifier 7A (7A—1, 7A—2...7A—n), a gain control circuit (AGC) 7B (7B—1, 7B—2...7B—n), an analog/digital converter 7C (7C—1, 7C—2...7C—n), a shift register 7D (7D—1, 7D—2...7D—n) serving as a receiving delay circuit, and an adder 7E.

The preamplifier 7A (7A—1, 7A—2...7A—n) receives an echo signal from the transducer element 1—1 (1—2...1—n) of the array probe 1, and amplifies the received echo signal up to a level suitable for signal processing in rear-stage circuits such as AGC circuit 7B, etc.

The gain control circuit 7B (7B—1, 7B—2...7B—n) is designed to attain a low gain in the B-mode, and attain a high gain in the D-mode. The switching of the gain level is effected when a mode signal, for example, is supplied from a control signal generating circuit 10 to the gain control circuit 7B.

The A/D converter 7C (7C—1, 7C—2...7C—n) converts the gain-controlled echo signal of each channel obtained from the gain control circuit 7B (7B—1, 7B—2...7B—n), as shown in FIG. 2, to a digital signal. The shift register 7D (7D—1, 7D—2...7D—n), which serves as the receiver delay circuit, temporarily stores the digital echo signal output from the A/D converter 7C (7C—1, 7C—2...7C—n). In accordance with the transmission delay control, the echo signal is read out from the shift register 7D at a readout timing corresponding to a delay time determined based on a beam deflection angle in the transmission focusing or the sector scanning. This readout operation is substantially regarded as a receiver delay control operation. The adder 7E adds the delayed echo signals supplied from the respective channels in a digital manner, and outputs the added value to the B-mode processor circuit 8 or the D-mode processor circuit 9.

The B-mode processor circuit 8 comprises an envelope detecting circuit 8A constituted by an absolute circuit and a low-pass filter, and a logarithmic conversion table 8B constituted by a read-only memory (ROM) or the like. The envelope detecting circuit 8A detects an envelope of the added echo signal. The logarithmic conversion table 8B subjects the amplitude of a envelope detection signal output from the envelope detecting circuit 8A to logarithmic conversion, and allows the resulting conversion signal to be stored in the frame memory 6A of the video processor circuit 6.

The D-mode processor circuit 9 comprises re-sampling circuits 9Aa and 9Ab for realizing a digital-mode orthogonal phase detection, MTI (Moving Target Indicator) filters 9Ba and 9Ab for eliminating clutter components, and an arithmetic circuit 9C including an FFT (Fast Fourier Transformation) arithmetic circuit for computing blood flow data, a correlation arithmetic circuit for computing an CFM image, etc. The re-sampling circuits 9Aa and 9Ab produce two orthogonal phase detection signals from the added echo signal with use of two sampling pulses having phases differing from each other by $\pi/2$. The MTI filters 9Ba and 9Bb eliminate from the two orthogonal phase detection signals clutter components included in Doppler shift components of the orthogonal phase detection signals and produced by motion of the heart or the wall of blood vessel. In the arithmetic circuit 9C, the FFT arithmetic circuit computes blood flow data such as the average velocity or variance of blood flow, by frequency-analizing the input signals from the MTI filters 9Ba and 9Bb, and outputs the computed blood flow data to the frame memory 6A. Also, the correlation arithmetic circuit included in the arithmetic circuit 9C computes the data relating to the velocity, direction and location of a blood flow by means of an autocorrelation process, and subjects the computed data to a coloring process, thus producing the CFM image data. The CFM image data is stored in the frame memory 6A.

With reference to FIG. 2, the gain control circuit 7B (7B—1, 7B—2...7B—n) will now be described in detail. The gain control circuit 7B (7B—1, 7B—2...7B—n) comprises an attenuator 21 having an attenuation degree of $\xi$dB, and an electronic switch 22 having contacts B and D, one of which is selected by a control signal from the control signal generating circuit 10. In the B-mode operation, the contact B of electronic switch 22 is selected, and an output from the preamplifier 7A is supplied to the A/D converter 7C through the attenuator 21. In the D-mode operation, the contact D of electronic switch 22 is selected, and the output of the preamplifier 7A is directly delivered to the A/D converter 7C.

Prior to a description of the operation of the apparatus according to this embodiment, a B-mode tomographic image signal (hereinafter, referred to as "B-mode signal") and a D-mode Doppler signal (hereinafter, referred to as "D-mode signal") will be described.

The B-mode signal corresponds to ultrasonic waves reflected from a sectional plane of a subject. Thus, the B-mode signal has a relatively high intensity, that is, the B-mode signal is a high-level signal. On the other hand, the D-mode signal corresponds to Doppler components of ultrasonic waves reflected from blood cells. Thus, the intensity of the D-mode signal is much lower than that of the B-mode signal, that is, the D-mode signal is a low-level signal. It is not necessary to obtain the B-mode signal and the D-mode signal simultaneously. These signals may be processed individually. The dynamic ranges for the B-mode and D-mode signals may be set separately. For example, as shown in FIG. 3, if the total dynamic range of the B-mode and D-mode signals is "A+B", the range A is assigned to the B-mode signal, and the range B is assigned to the D-mode signal. If the dynamic range is divided to two ranges for the B-mode and D mode signals and these signals are processed separately, it becomes possible to process these signals by using a general circuit element having a narrow dynamic range, so that a diagnostic image which is fully satisfactory in practical aspects may be obtained.

More specifically, the B-mode signal is obtained from a region having a high ultrasonic reflectivity, such as bones or internal organs. In such a region, no blood flow is substantially observed. Thus, a D mode image of suitable contrast can be obtained by appropriately amplifying the weak D-mode signal and saturating the B-mode signal.

A boundary of the range A for the B-mode signal and the range B for the D-mode signal is not clear. In other words, they are slightly overlapped or separated. For example, as shown in a middle part of FIG. 3, if the total dynamic range is $(\alpha+\beta+\gamma)$dB, the dynamic range of the B-mode signal is $\alpha$dB, and the dynamic range of the D-mode signal is $\gamma$dB which is lower than the lower limit of the range of the B-mode signal by $\beta$dB. The mode-signal includes a Doppler shift signal representative of the motion of blood cells and a clutter component representative of the motion of the heart or the wall of blood vessel. There is a case where the level of the clutter component becomes equal to the lowest level of the B-mode signal (or these may be overlapped, as indicated by dashed lines in FIG. 3). When the signals of these dynamic ranges are to be processed, it is necessary that the A/D converter 7C (7C—1, 7C—2...7-C—n) have a dynamic range of at least $\delta$dB dynamic range. The reason for this is that, in order to obtain the Doppler shift signal without saturating the B-mode signal, the clutter component on which the Doppler shift signal is superposed needs to be digitized without saturating the clutter component.

The B-mode signal, which has been passed through the attenuator 21, is processed with the range A shown in FIG. 3. On the other hand, the D-mode signal which has not been passed through the attenuator 21 is processed within the range B shown in FIG. 3 which covers both the Doppler shift signal and the clutter component.

The operation of the ultrasonic imaging apparatus shown in FIG. 1 will now be described.

Figure 4:
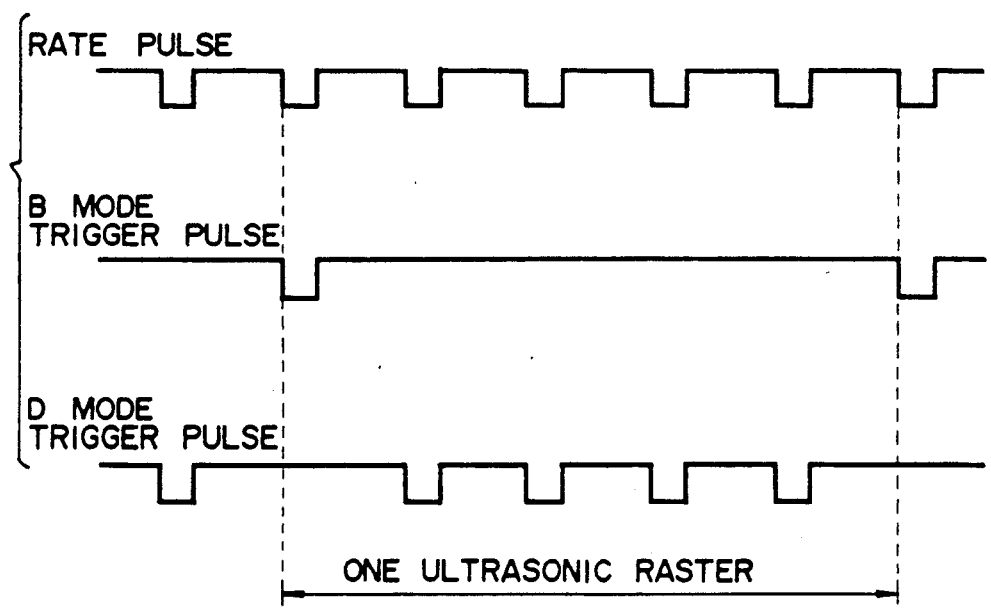
FIG. 4 is a timing chart for illustrating the operation of the ultrasonic imaging apparatus.

First, an operator selects, for example, a sector scan mode, and sets the focal depth (single-stage focus) and diagnostic condition of displaying an image obtained by superposing a tomographic image and a CFM (color flow map) image. Under this condition, the apparatus is operated by a control signal fed from the control signal generating circuit 10, in accordance with the timing shown in FIG. 4. In this case, the dynamic range of the B-mode signal and that of the D-mode signal are related to each other, as shown in FIG. 4.

The pulse generator 2A outputs a rate pulse. Five rate pulses forms a one ultrasonic raster. When the first rate pulse is generated, the electronic switch 22 of the gain control circuit 7B is operated to select the contact B in response to a control signal fed from the control signal generating circuit 10. Consequently, an echo signal (B-mode signal) is attenuated by the attenuator 21 by a degree of dB. The attenuated signal is supplied to the A/D converter ξ7C and converted to a digital signal. At this time, the gain level of the variable gain type preamplifier 7A is manually adjusted, so that the amplitude of the B-mode signal passing through the attenuator 21 may match with the input range of the A/D converter 7C. The attenuated B-mode signal is digitized over its entire dynamic range. The digitized B-mode signals of the respective channels are added by the adder 7E, and the added signal is input to the B-mode processor circuit 8. Based on the added signal, the B-mode processor circuit 8 produces tomographic image data. The tomographic image data is stored in the frame memory 6A of the video processor circuit 6.

When the second rate pulse is generated, the electronic switch 22 of the gain control circuit 7B is operated to select the contact D. The echo signal (D-mode signal) is not attenuated by the gain control circuit 7B and directly input to and digitized by the A/D converter 7C. In this case, most of the amplitude of the D-mode signal falls within the input range of the A/D converter 7C.

After all digitized D-mode signals are added, the added signal is input to the D-mode processor circuit 9. In the D-mode processor circuit 9, the re-sampling circuits 9A$a$ and 9A$b$ convert the added signal to two orthogonal phase detection signals. The orthogonal phase detection signals are caused to flow through the MTI filters 9B$a$ and 9B$b$ and clutter components thereof are eliminated. The output signals of the MTI filters are supplied to the arithmetic circuit 9C. The arithmetic circuit 9C produces blood flow data such as the average velocity, variance, etc. of blood flow, based on the input signals. This operation is repeated upon the generation of the third, fourth and fifth pulses, so that four Doppler shift data units are obtained with respect to the same position. Based on the four Doppler shift data units, CFM image data regarding a predetermined deflection angle position of the beam is calculated. The obtained CFM image data is input to the frame memory 6A of the video processor circuit 6 and superposed on the tomographic image previously stored in the frame memory 6A. Thus, superposed image data is formed in the memory 6A.

According to the above embodiment, the gain level of the gain control circuit 7B provided at the front stage of the A/D converter 7C of the digital receiver circuit is changed in accordance with the B-mode or the D-mode. Thus, the B-mode signal and the D-mode signal having amplitudes corresponding to the input range of the A/D converter 7C can be produced (the B-mode signal is attenuated, but the D-mode signal is not).

More specifically, the B-mode signal is attenuated by the attenuator so as to have the amplitude substantially equal to that of the D-mode signal. By using the A/D converter 7C having the input range matching with the amplitude of the output of the preamplifier 7A in the D-mode, both B-mode and D-mode signals can be digitized. In other words, in the prior art, in order to process the echo signals, an n-number of A/D converters 7B each having a dynamic range of 14 bits or more are required. In contrast, in this embodiment, the echo signals can be processed by the A/D converters each having a narrow dynamic range of about 8 bits.

In particular, there is a tendency that the sampling frequency of an A/D converter used in an ultrasonic receiving process increases more and more, and the number of channels also increases more and more. Under the circumstances, it is very advantageous in the field of ultrasonic imaging to digitize the echo signals by using general-purpose A/D converters of 8 bits or thereabouts.

Figure 5:
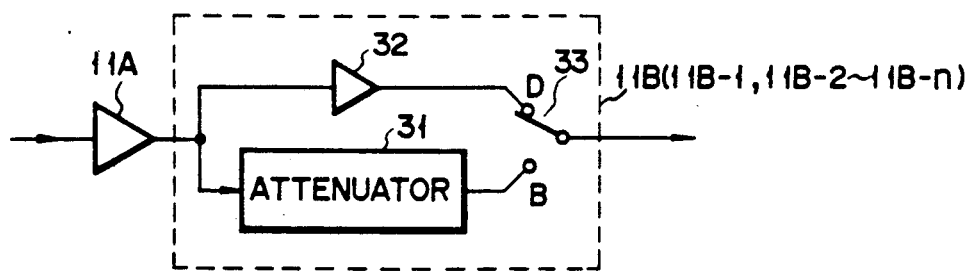
FIG. 5 shows another gain control circuit used in the apparatus shown in FIGS. 1A and 1B.

FIG. 5 shows a modification of the gain control circuit.

The gain control circuit 11B (11B—1, 11B—2,...11-B—n) corresponding to those 7B (7B—1, 7B—2...7-B—n) in FIG. 1A comprises an attenuator 31, a variable gain type amplifier 32, and an electronic switch 33 which is operated to select one of contacts B and D in response to a control signal from the control signal generator 10. In the B-mode operation, the electronic switch 33 is caused to select the contact B, so that an output of the preamplifier 11A (corresponding to the preamplifier 7A) passes through the attenuator 31 and goes to the A/D converter 7C. In the D-mode operation, the electronic switch 33 is let to select the contact D, so that the output of the preamplifier 11A is supplied to the variable gain type amplifier 32 and then input to the A/D converter 7C.

The gain of the B-mode signal is controlled by the preamplifier 11A and the attenuator 31 and the gain of the D-mode signal is controlled by the preamplifier 11A and the variable gain type amplifier 32, so as to match with the input range of the A/D converter 7C. At the same time as the B-mode is switched to D-mode, or vice versa, the control signal from the control signal generating circuit 10 controls the operation of the electronic switch 33 and also the gains of the preamplifier 11A and variable gain type amplifier 32.

In the above embodiment, a low-pass filter for restricting an input signal band may be provided in order to prevent cyclical noise. This low-pass filter may be provided between the preamplifier 7A (11A) and the A/D converter 7C.

The direction of beams may differ between the B-mode and the D-mode. Unless the B-mode and D-mode signals are mutually used as in the prior art, the operation timing is not limited to the timing shown in FIG. 4. The present invention is applicable to an apparatus employing an annular array probe.

As described above, in the present invention, the gain control circuit for controlling the gain of the received signal is provided at the front stage of the circuit for digitizing the received signal. Thus, the amplitudes of the B-mode and D-mode signals can be independently made to match with the A/D input range, and, consequently, an A/D converter of a narrow dynamic range can be used in each receiving channel.

The present invention can provide an ultrasonic imaging apparatus wherein the precision in the receiving circuit is varied in accordance with the tomographic image mode or the Doppler mode, thus enhancing directional characteristics and resolution.

The present invention may be applied to an ultrasonic imaging apparatus provided with an ultrasonic transducer having a single ultrasonic transducer element or a mechanical scanning type ultrasonic transducer having a single ultrasonic transducer element or an array of a plurality of ultrasonic transducer elements.

What is claimed is:

1. An ultrasonic imaging apparatus comprising:
   means for selecting a B-mode for obtaining a tomographic image and a D-mode for obtaining Doppler data;
   ultrasonic transducer means, constituted by at least one ultrasonic transducer element, for outputting an ultrasonic beam and converting an echo wave of the ultrasonic beam to a B-mode echo signal corresponding to the B-mode or a D-mode echo signal corresponding to the D-mode;
   transmitting means, connected to said ultrasonic transducer means, for supplying a drive pulse to the transducer element, to generate the ultrasonic beam;
   receiving means, connected to said ultrasonic transducer means, including gain control means for controlling the gain of at least one of the B-mode and D-mode echo signals output from said transducer means so as to equalize the level of the B-mode echo signal to that of the D-mode echo signal and outputting a gain-controlled echo signal, and conversion means for converting the gain-controlled echo signal to a received signal;
   B-mode processing means, connected to said receiving means, for producing a B-mode image signal from said received signal;
   D-mode processing means, connected to said receiving means, for producing Doppler data from said received signal; and
   display means, connected to said B-mode processor means and said D-mode processor means, for displaying the B-mode image signal and the Doppler data.

2. The ultrasonic imaging apparatus according to claim 1, wherein said gain control means includes attenuation means for attenuating said B-mode echo signal so that the level of the B-mode echo signal is made equal to that of the D-mode echo signal.

3. The ultrasonic imaging apparatus according to claim 2, wherein said gain control means comprises passing means for passing the D-mode echo signal, and switching means for selecting one of said attenuation means and said passing means.

4. The ultrasonic imaging apparatus according to claim 1, wherein said gain control means includes means for attenuating said B-mode echo signal and means for amplifying D-mode echo signal, both means attenuating the B-mode signal and amplifying the D-mode signal so that the levels of the B-mode and D-mode signals become equal to each other.

5. The ultrasonic imaging apparatus according to claim 4, wherein said gain control means comprises switching means for selecting one of said attenuating means and said amplifying means.

6. The ultrasonic imaging apparatus according to claim 1, wherein said display means includes a frame memory for superposing the B-mode image signal and the Doppler data upon each other, and storing the superposed data.

7. The ultrasonic imaging apparatus according to claim 1, wherein said D-mode processor means calculates blood flow data and color flow map data, based on said received signal.

8. The ultrasonic imaging apparatus according to claim 7, wherein said D-mode processor means includes means for sampling said received signal by using two sampling pulses having phases differing by $\pi/2$ and for producing two orthogonal phase detection signals, and filter means for eliminating clutter components from said orthogonal phase detection signals.

9. The ultrasonic imaging apparatus according to claim 1, wherein said ultrasonic means comprises an array of a plurality of ultrasonic transducer elements.

10. An ultrasonic imaging apparatus comprising:
    means for selecting a B mode for obtaining a tomographic image and a D-mode for obtaining Doppler data;
    ultrasonic transducer means, constituted by an array of a plurality of ultrasonic transducer elements, for radiating ultrasonic beams to a subject and converting echo waves of the ultrasonic beams reflected from the subject to a B-mode echo signal corresponding to the B-mode and a D-mode echo signal corresponding to the D-mode;
    transmitting means, connected to said ultrasonic transducer means, for supplying respective drive pulses to the transducer elements to generate the ultrasonic beams which are converged at a predetermined position and scan the subject in a predetermined scanning mode;

receiving means, connected to said ultrasonic transducer means, including a plurality of gain control means each for controlling the gain of each of the B-mode and D-mode echo signals output from said transducer elements so as to equalize the level of the B-mode echo signal to that of the D-mode echo signal and for outputting each gain-controlled echo signal, a plurality of conversion means each for converting the gain-controlled echo signal to a digital signal, and delay/adding means for delaying the digital signals output from said conversion means in accordance with said convergence and scanning mode and adding them to produce a received signal;

B-mode processing means, connected to said receiving means, for producing a B-mode image signal from said received signal;

D-mode processing means, connected to said receiving means, for producing Doppler data from said received signals; and display means, connected to said B-mode processor means and said D-mode processor means, for displaying the B-mode image signal and the Doppler data.

11. The ultrasonic imaging apparatus according to claim 10, wherein each of said gain control means includes means for attenuating said B-mode echo signal so that the level of the B-mode echo signal is made equal to that of the D-mode echo signal.

12. The ultrasonic imaging apparatus according to claim 11, wherein each of said gain control means comprises passing means for passing the D-mode echo signal, and switching means for selecting one of said attenuating means and said passing means.

13. The ultrasonic imaging apparatus according to claim 10, wherein each of said gain control means includes means for attenuating said B-mode echo signal and means for amplifying D-mode echo signal, both means attenuating the B-mode signal and amplifying the D-mode signal so that the levels of the B-mode and D-mode signals become equal to each other.

14. The ultrasonic imaging apparatus according to claim 13, wherein said gain control means comprises switching means for selecting one of said attenuating means and said amplifying means.

15. The ultrasonic imaging apparatus according to claim 10, wherein said display means includes a frame memory for superposing the B-mode image signal and the Doppler data upon each other, and storing the superposed data.

16. The ultrasonic imaging apparatus according to claim 10, wherein said D-mode processor means calculates blood flow data and color flow map data, based on said received signal.

17. The ultrasonic imaging apparatus according to claim 16, wherein said D-mode processor means includes means for sampling said received signal by using two sampling pulses having phases differing by $\pi/2$ and for producing two orthogonal phase detection signals, and filter means for eliminating clutter components from said orthogonal phase detection signals.

* * * * *